United States Patent [19]

Widlund

[11] Patent Number: 4,880,421
[45] Date of Patent: Nov. 14, 1989

[54] DISPOSABLE ABSORBENT ARTICLE SUCH AS A DIAPER OR AN INCONTINENCE PROTECTOR

[75] Inventor: Urban Widlund, Mölnlycke, Sweden

[73] Assignee: Molnlycke AB, Goteborg, Sweden

[21] Appl. No.: 123,949

[22] Filed: Nov. 23, 1987

[30] Foreign Application Priority Data

Nov. 26, 1986 [SE] Sweden ............................ 8605069

[51] Int. Cl.⁴ .............................................. A01F 13/16
[52] U.S. Cl. .................................. 604/385.2; 604/389
[58] Field of Search ................. 604/358, 385.1, 385.2, 604/387, 389, 390, 393, 394, 396, 398386

[56] References Cited

U.S. PATENT DOCUMENTS 4,568,344 2/1986 Suzuki et al. ....................... 604/389
4,578,071 3/1986 Buell ................................... 604/385

FOREIGN PATENT DOCUMENTS 8800442 1/1988 PCT Int'l Appl. ................... 601/358

Primary Examiner—Max Hindenburg
Assistant Examiner—K. M. Reichle
Attorney, Agent, or Firm—Young & Thompson

[57] ABSTRACT

The present invention relates to a disposable absorbent article (1) such as a diaper or an incontinence protector intended during use to seal like a pant around the user's abdomen and comprising an absorption body (4) applied between a liquid impermeable outer layer (2) facing away from the user and a liquid permeable inner layer (3) facing the user, these two layers being interconnected at least along the long sides of the article. The inventive article is primarily distinguished in that a strip (13,14) of a liquid impermeable material, extending in the transverse direction of the article, is disposed at least at one end portion of the article, this strip having a portion (16,17) positioned between the absorption body (4) and the liquid permeable inner layer (3) and a portion (18,19) folded over the end edge (10,15) of the absorption body while being secured to the liquid impermeable outer layer (2), the article thereby obtaining a liquid-tight reinforced edge portion (22,23).

4 Claims, 3 Drawing Sheets

DISPOSABLE ABSORBENT ARTICLE SUCH AS A DIAPER OR AN INCONTINENCE PROTECTOR

FIELD OF THE INVENTION

The present invention relates to a disposable absorbent article such as a diaper or an incontinence protector which is intended during use to seal like a pant around the user's abdomen and which comprises an absorbent body positioned between a liquid impermeable outer layer facing away from the user and a liquid permeable inner layer facing the user, said layers being joined together at least along the long sides of the article.

BACKGROUND OF THE INVENTION

As an example of articles of this type can be mentioned the so-called all-in-one diapers. Normally, such diapers have a narrow crotch portion and two end portions of substantially wider dimensions than the crotch portion. In the following, one of these end portions is referred to as the belly portion and the other as the seat portion, said two portions being fixed together at the sides by means of tape tabs for obtaining the pant-like fit about the user's abdomen. Beyond the tape tabs there are required for this type of pants no additional attachment means such as special baby pants or diaper backings.

When designing diapers, the most significant problem is generally associated with the effort of providing high security against urine leakage at the leg linings and waist edge of the diaper. The first-mentioned type of leakage is preferably avoided by using elastic members making the diaper edges seal tightly about the user's legs.

Leakage at the waist edge primarily occurs when the user is lying down because of gaps then being formed between the diaper and the user's back or belly. Due to the thickness and the relative stiffness of the absorption body, such gaps are difficult to avoid even with diapers having elastic members at the waist edge. With the user's comfort in mind, the stretching force cannot be allowed to exceed a certain degree.

As another way of reducing waist leakage there is previously described a method of folding a portion of the liquid impermeable outer layer over the end edges of the absorption body and a distance in over it, between the absorption body and the liquid permeable inner layer on the side facing the user. In this manner body fluid is prevented from being led out over the diaper edges by the absorbent material or the liquid permeable inner layer.

In the manufacture of diapers having a bent-over edge of liquid-tight material at the waist lining, a preshaped absorption body is applied to the liquid-tight outer layer which is normally made of a plastic film, whereafter folding takes place and the liquid permeable inner layer is applied in a manner so as to cover the bent-over portions of the liquid-tight outer layer as well. In the production of the prior art diapers having a bent-over plastic edge this is a necessary procedure in order for the entire diaper surface facing the user's skin during use to be covered with the liquid permeable inner layer, and because this layer is conventionally a fiber fabric layer the user's skin will be prevented from direct contact with the bent-over plastic portions As already mentioned, such an all-in-one diaper is fixed together with the aid of tape tabs coated with a pressure-sensitive glue, said tabs being applied to the side edges of the seat portion. When the diaper is put on, the tape tabs are brought forward and in over the belly portion for attachment thereto. However, the liquid impermeable outer layer of the diaper constituting the diaper outside during use is most often made of a thin polyethylene film which is easily ruptured when subjected to tensile stresses. In order to avoid rupture and for enabling the diaper to be opened and resealed by means of the tape tabs it is previously known to provide the upper part of the outer layer of the diaper belly portion with a somewhat stiffer reinforcing plastic strip.

BRIEF SUMMARY OF THE INVENTION

With the present invention there has been achieved an improved absorbent article of the type set forth in the introduction. The inventive article is primarily distinguished in that a strip made of a liquid impermeable material and extending in the transverse direction of the article is arranged at least at one end portion thereof, said strip having a portion located between the absorption body and the liquid permeable inner layer as well as a portion which is folded over the edge of the absorption body and is secured to the liquid impermeable outer layer, the article thereby being given a liquid-tight reinforced edge portion. By the inventive method of folding strips of liquid impermeable material over the end edge of the article there is obtained not only a combination of a liquid barrier at the user's waist and a reinforced attachment area at the belly portion of the article for the tape tabs, but also a plurality of advantages with regard to manufacture.

In fact, the use of strips made of a liquid impermeable material such as plastic, for example, will enable a method of manufacture by means of which the absorption body in the article can be applied to the liquid permeable inner layer made of fiber fabric, for example, whereupon the liquid impermeable outer layer is applied over the absorption body.

Because the strips made of a liquid impermeable material are attachable to the liquid permeable inner layer before applying the absorption body thereto, a liquid-tight edge lining covered with this layer can be obtained even if the article is manufactured with the liquid permeable layer placed at the bottom. As the liquid permeable layer is of course also pervious to air, the absorption body of the article can be accomplished with airborne fibers by so-called mat formation on this layer. This is naturally not applicable to articles manufactured as described in the introduction and having a lowermost liquid and air impervious plastic layer, since the air supplied during the mat-forming process cannot then be sucked out through such a tight layer.

Another advantage associated with the production of absorbent articles of the type mentioned in the introduction and having a lowermost liquid permeable layer is that air may then be sucked out of the article through the liquid permeable inner layer subsequent to applying the liquid impermeable outer layer to the article. In this manner the article casing, i.e. the combined liquid permeable inner layer and the liquid impermeable outer layer surrounding the absorption body will be inclined to seal more snugly about the absorption body, increasing thereby its coherency during use of the article. To maintain a close contact between the casing and the absorption body during use of the article and to further increase the stability of the absorbent body, the casing may also be affixed to the absorbent body by means of so-called spray-gluing with hot melt, for example.

According to one embodiment of the invention, the extent of the liquid permeable inner layer in the longitudinal direction of the article corresponds essentially to that of the absorption body.

According to another embodiment of the invention, at least one strip of liquid impermeable material is made elastic.

According to a further embodiment of the invention, the portion of the liquid impermeable strip which is bent in over the edge of the absorption body is in liquid-tight contact with a portion of the liquid impermeable outer layer, said two portions together being folded over the absorption body edge while being attached to the liquid impermeable layer on the side of the article facing away from the user.

BRIEF DESCRIPTION OF THE DRAWINGS

The invention will be described in more detail below with reference to an exemplary embodiment shown in the accompanying drawings, of which

DETAILED DESCRIPTION OF THE INVENTION

Figure 1:
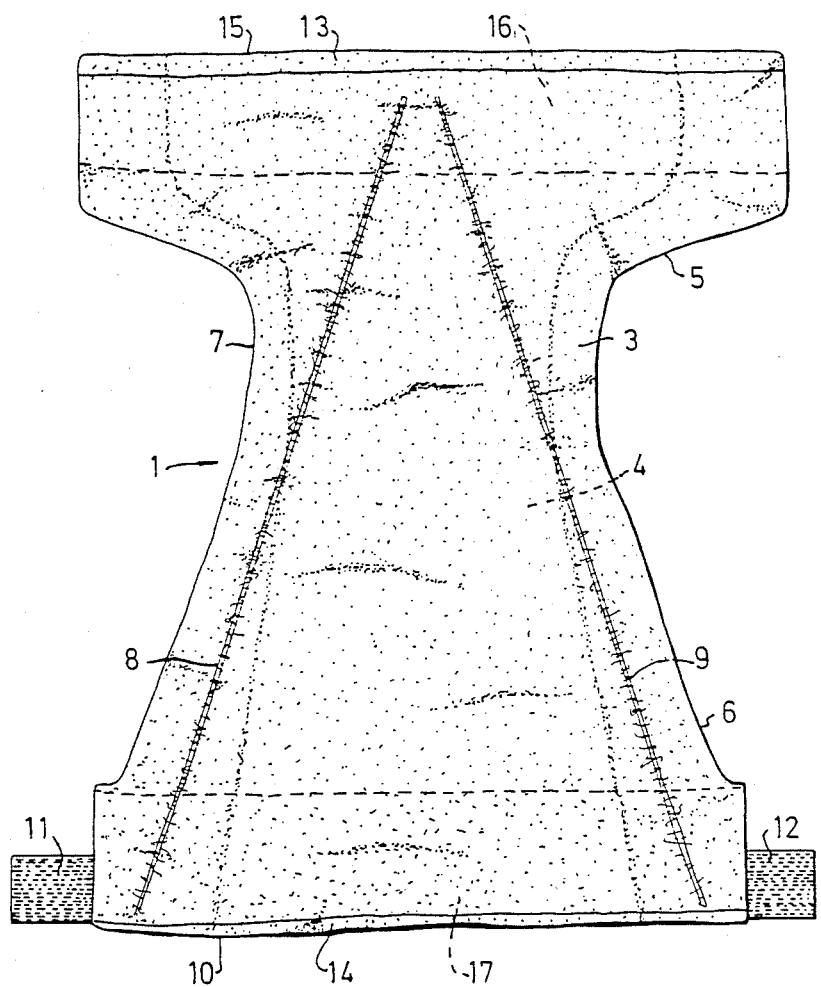
FIG. 1 is a first plan view of a diaper made according to the invention as seen from the side facing the user, referred to in the following as the inside.
Figure 2:
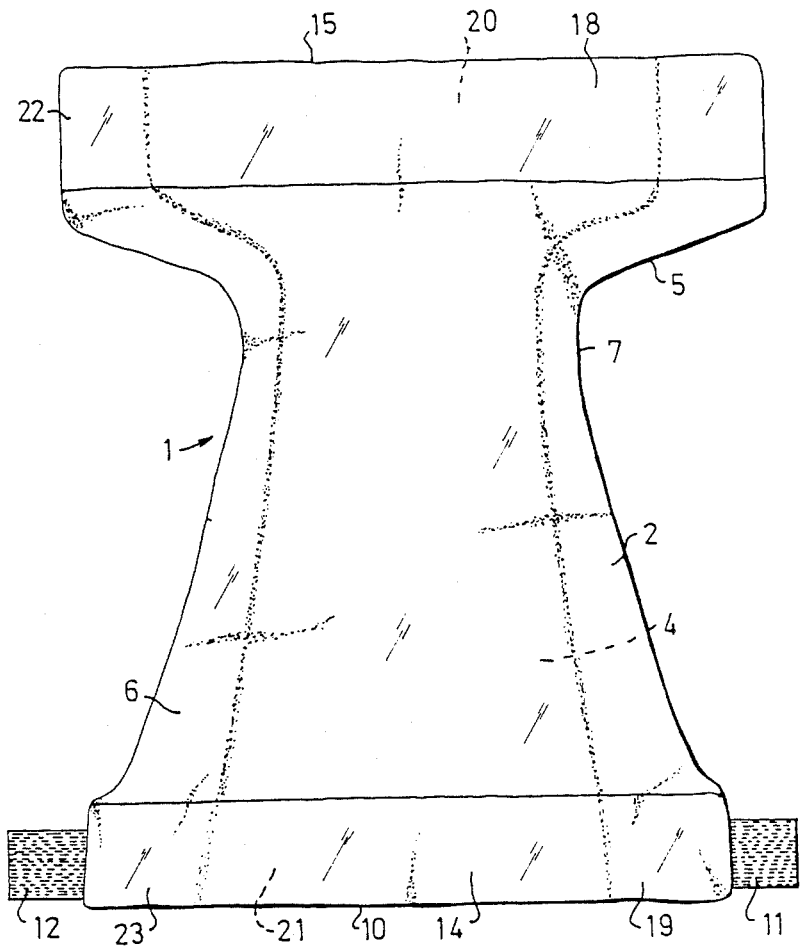
FIG. 2 is a second plan view of the diaper shown in FIG. 1 as seen from the side facing away from the user, referred to in the following as the outside.
Figure 3:
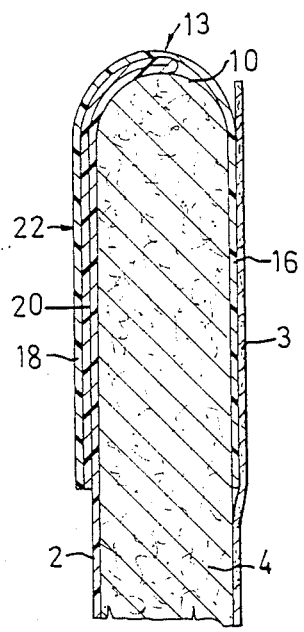
FIG. 3 is a cross-sectional view taken in the longitudinal direction of the diaper through the area closest to one of its transverse edges.

The diaper 1 illustrated in the drawings is a so-called all-in-one diaper comprising a liquid-tight outer layer 2 of polyethylene film on the outside of the diaper, a liquid permeable inner layer 3 of fiber fabric on the inside of the diaper, and an intermediate absorption body 4 of cellulose fluff pulp. The diaper has two wide portions: the belly portion 5 and the seat portion 6, intended to be applied over the user's belly and seat, respectively. Between the belly portion 5 and the seat portion 6 there is a narrow so-called crotch portion 7 intended to be positioned between the user's legs.

The diaper 1 is further provided with elastic members 8, 9 applied in the form of a V between the absorption body 4 and the liquid permeable fiber fabric layer or inner layer 3. On either side of the seat portion 6 and close to the waist edge 10 on the rear side during use of the diaper 1, there are attached two tape tabs 11, 12 serving as fastening means when applying the diaper onto the user's body.

According to the invention, strips 13, 14 made of a liquid-tight material, preferably plastic, are folded around the diaper waist edges 10, 15 of the belly and seat portions 5 and 6, respectively. Due to the liquid-tight strips bent in over the waist edges there is obtained, when applying the diaper onto the user's body, a liquid-impermeable lining around the waist opening of the diaper. According to the invention, the liquid-tight plastic strips 13, 14 are in fact applied with their respective portion 16 and 17 onto the diaper inside between the absorption body 4 and the liquid permeable fiber fabric layer 3 while simultaneously having their respective portions 18 and 19 connected to the respective portions 20 and 21 of the liquid impermeable plastic layer 2 which extend past the absorption body 4, the portions 18, 19 and 20, 21 together being folded over the diaper waist edges 10 and 15, respectively, while being secured to the liquid impermeable plastic layer 2 on the outside of the diaper. In this manner the plastic layer 2 on the diaper outside will be given a reinforced area 22 and 23, respectively, at each of the two waist edges 10 and 15, said area having three interconnected plastic layers 2, 20, 18 and 2, 21, 19, respectively. To advantage, the three layers 2, 20, 18 and 2, 21, 19 may be united by means of so-called spray-gluing with hot melt so as to effectively create liquid-tight barriers at the diaper waist edges 10 and 15.

When applying the diaper illustrated in the drawings onto the user's body, the tape tabs 11, 12 secured to the seat portion 6 are used for fixing together the diaper at the sides so that it will seal in a pant-like manner around the user's abdomen. The elastic members 8, 9 in the form of covered threads, for example, will then simplify for the diaper to conform to the user's abdomen avoiding thereby leakage around the thighs.

For fixing the diaper together, the tape tabs 11, 12 are brought in over the belly portion 5 to be attached thereto within the area 22 which is reinforced by the plastic strip 13 folded over the waist edge 15 of the belly portion. The three united plastic layers 2, 20, 18 within this area 22 together constitute a reinforcement of the liquid impermeable outer plastic layer 2 which is strong enough to prevent ruptures therein during normal use of the diaper, caused by tensile stresses occurring on securement of the tape tabs. The reinforcement is also sufficiently strong for the tape tabs to be loosened from the plastic strip portion 18 within the area 22 and refastened thereto without the risk of tearing the plastic material.

Although the embodiment described herein relates to a diaper having bent-over plastic strips at the waist edges of both the seat portion and the belly portion, the inventive idea also encompasses diapers having no such bent-over strip at either one of the two waist edges. As an example, it is possible to provide only the liquid impermeable layer on the outside of the belly portion with an area reinforced by means of a folded plastic strip, because the belly portion is where the tape tabs of the seat portion should have their securement when applying the diaper onto the user. However, such a reinforcement edge could to advantage be provided also at the waist lining of the seat portion, since the tape strips for attachment to the seat portion would then be more securely affixed.

The implementation of the invention does not require for the strips made of a liquid impermeable material to be folded over the end edges of the absorption body together with portions of the liquid impermeable outer layer. However, if the longitudinal extension of this layer essentially corresponds to that of the absorption body, there are obtained merely two layers of material within the areas on the outsides of the article reinforce by the strips, but in many cases this would still provide a sufficient degree of tensile strength for the liquid impermeable outer layer. Furthermore, a heavier material could be chosen for the strips should additional tensile strength be desirable.

Although the strips of liquid impermeable material have been referred to above as "plastic strips", it is understood that strips of other elastic and rubber-like materials could be conceived since it may naturally be preferable to utilize at least one elastic strip for the diaper to seal more effectively around the user's waist.

Finally, the strips could alternatively be made of a foamed, liquid-tight material for increasing the user's comfort and for enhancing the stability of the article.

The invention is not restricted to the exemplary embodiment described herein, but a plurality of modifications are conceivable within the scope of the patent claims.

I claim:

1. A disposable absorbent article such as a diaper or an incontinence protector, having pressure-adhesive tape tabs for securing the article in a pant-like manner around the user's waist, the article being elongated and having opposite ends and longitudinal sides extending between said opposite ends, the article comprising an absorption body, a liquid impermeable outer layer on one side of the absorption body and a liquid permeable inner layer on the other side of the absorption body, said layers being united at least along said longitudinal sides, said pressure-adhesive tape tabs being disposed at one end of the article and being adapted to contact the other end of the article when securing the article about the user' waist, on the same side of the article as said liquid impermeable outer layer, and a strip of liquid permeable material extending transversely of the length of the article at least at said other end of the article, said strip having a portion secured between the absorption body and the liquid permeable inner layer and a portion which extends over a transverse edge of the absorption body at said other end and is directly secured to the liquid impermeable outer layer on the side of the liquid impermeable outer layer opposite the absorbent body, whereby the article has a reinforced attachment area where the liquid impermeable outer layer and said strip overlap and are directly secured together, for receiving the tape tabs, and a liquid impermeable lining around at least part of the waist opening of the article.

2. An article according to claim 1, in which the length of the liquid permeable inner layer is substantially the same as the length of the absorbent body.

3. An article according to claim 1, in which said at least one strip is of elastic material.

4. An article according to claim 1, in which said liquid impermeable outer layer is folded back in a double thickness on itself beneath said strip.

* * * * *